US010932790B2

(12) United States Patent
Baril et al.

(10) Patent No.: US 10,932,790 B2
(45) Date of Patent: Mar. 2, 2021

(54) GEARED ACTUATION MECHANISM AND SURGICAL CLIP APPLIER INCLUDING THE SAME

(71) Applicant: Covidien LP, Mansfield, MA (US)

(72) Inventors: Jacob C. Baril, Norwalk, CT (US); Christopher W. Kaswer, Avon, CT (US); Brian J. Creston, West Haven, CT (US); Thomas A. Zammataro, Hamden, CT (US); Matthew A. Dinino, Newington, CT (US)

(73) Assignee: COVIDIEN LP, Mansfield, MA (US)

( * ) Notice: Subject to any disclaimer, the term of this patent is extended or adjusted under 35 U.S.C. 154(b) by 359 days.

(21) Appl. No.: 16/031,027

(22) Filed: Jul. 10, 2018

(65) Prior Publication Data
US 2019/0046203 A1    Feb. 14, 2019

Related U.S. Application Data

(60) Provisional application No. 62/542,335, filed on Aug. 8, 2017.

(51) Int. Cl.
| A61B 17/128 | (2006.01) |
| A61B 17/00 | (2006.01) |
| A61B 17/29 | (2006.01) |

(52) U.S. Cl.
CPC ........ *A61B 17/128* (2013.01); *A61B 17/1285* (2013.01); *A61B 2017/0023* (2013.01);
(Continued)

(58) Field of Classification Search
CPC ... A61B 17/128; A61B 17/1285; A61B 17/28; A61B 2017/0023; A61B 2017/00367;
(Continued)

(56) References Cited

U.S. PATENT DOCUMENTS

| 3,120,230 A | 2/1964 | Skold |
| 3,363,628 A | 1/1968 | Wood |

(Continued)

FOREIGN PATENT DOCUMENTS

| AU | 2013254887 A1 | 11/2013 |
| CA | 1163889 A | 3/1984 |

(Continued)

OTHER PUBLICATIONS

Extended European Search Report corresponding to Patent Application EP 18154617.7 dated Jun. 25, 2018.

(Continued)

*Primary Examiner* — Mohamed G Gabr

(57) ABSTRACT

An actuation mechanism, and a handle assembly and a surgical clip applier including the same are disclosed. The actuation mechanism includes a drive bar movable through a stroke having first and second stroke portions and an output gear rack. First and second intermediate gears include input portions operably coupled to a trigger and output portions defining different diameters. In the first stroke portion, the output portion of the first intermediate gear is engaged with the gear rack such that the first intermediate gear drives the drive bar. In the second stroke portion, the output portion of the second intermediate gear is disposed in engagement with the gear rack such that the second intermediate gear drives the drive bar. A different mechanical advantage is provided in the first portion of the stroke length as compared to the second portion of the stroke length.

20 Claims, 5 Drawing Sheets

(52) U.S. Cl.
CPC ............... *A61B 2017/0046* (2013.01); *A61B 2017/00367* (2013.01); *A61B 2017/00407* (2013.01); *A61B 2017/2912* (2013.01); *A61B 2017/2923* (2013.01)

(58) Field of Classification Search
CPC .. A61B 2017/00407; A61B 2017/0046; A61B 2017/2912; A61B 2017/2923; A61B 2017/2932
See application file for complete search history.

(56) References Cited

U.S. PATENT DOCUMENTS

| | | |
|---|---|---|
| 3,638,847 A | 2/1972 | Noiles et al. |
| 3,675,688 A | 7/1972 | Bryan et al. |
| 3,735,762 A | 5/1973 | Bryan et al. |
| 3,867,944 A | 2/1975 | Samuels |
| 4,226,242 A | 10/1980 | Jarvik |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |
| 4,418,694 A | 12/1983 | Beroff et al. |
| 4,471,780 A | 9/1984 | Menges et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,726,372 A | 2/1988 | Perlin |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,796,625 A | 1/1989 | Kees, Jr. |
| 4,799,481 A | 1/1989 | Transue et al. |
| 4,815,466 A | 3/1989 | Perlin |
| 4,821,721 A | 4/1989 | Chin et al. |
| 4,822,348 A | 4/1989 | Casey |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,931,058 A | 6/1990 | Cooper |
| 4,934,364 A | 6/1990 | Green |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,563 A | 11/1991 | Green et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,356,064 A | 10/1994 | Green et al. |
| 5,359,993 A | 11/1994 | Slater et al. |
| 5,366,458 A | 11/1994 | Korthoff et al. |

(56) References Cited

U.S. PATENT DOCUMENTS

| | | |
|---|---|---|
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro |
| 5,383,880 A | 1/1995 | Hooven |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,448,042 A | 9/1995 | Robinson et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,562,655 A | 10/1996 | Mittelstadt et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,743,310 A | 4/1998 | Moran |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,991 A | 7/1999 | Whitehead et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,044,971 A | 4/2000 | Esposito et al. |
| 6,045,560 A | 4/2000 | McKean et al. |
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |

(56) References Cited

U.S. PATENT DOCUMENTS

| | | |
|---|---|---|
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,562,051 B1 | 5/2003 | Bolduc et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,733,514 B2 | 5/2004 | Miser |
| 6,743,240 B2 | 6/2004 | Smith et al. |
| 6,743,241 B2 | 6/2004 | Kerr |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,821,285 B2 | 11/2004 | Laufer et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,676 B2 | 5/2005 | Zubok et al. |
| 6,896,682 B1 | 5/2005 | McClellan et al. |
| 6,896,684 B2 | 5/2005 | Monassevitch et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,916,332 B2 | 7/2005 | Adams |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,001,399 B2 | 2/2006 | Damarati |
| 7,037,315 B2 | 5/2006 | Sancoff et al. |
| 7,041,119 B2 | 5/2006 | Green |
| 7,052,504 B2 | 5/2006 | Hughett |
| 7,056,330 B2 | 6/2006 | Gayton |
| 7,070,602 B2 | 7/2006 | Smith et al. |
| 7,108,700 B2 | 9/2006 | Chan |
| 7,108,703 B2 | 9/2006 | Danitz et al. |
| 7,141,056 B2 | 11/2006 | Manetakis |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,213,736 B2 | 5/2007 | Wales et al. |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,238,191 B2 | 7/2007 | Bachmann |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,312,188 B2 | 12/2007 | Kiso |
| 7,316,693 B2 | 1/2008 | Viola |
| 7,316,696 B2 | 1/2008 | Wilson, Jr. et al. |
| 7,322,995 B2 | 1/2008 | Buckman et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,367,939 B2 | 5/2008 | Smith et al. |
| 7,407,074 B2 | 8/2008 | Ortiz et al. |
| 7,419,495 B2 | 9/2008 | Menn et al. |
| 7,422,137 B2 | 9/2008 | Manzo |
| 7,431,724 B2 | 10/2008 | Manetakis et al. |
| 7,452,327 B2 | 11/2008 | Durgin et al. |
| 7,485,124 B2 | 2/2009 | Kuhns et al. |
| 7,488,335 B2 | 2/2009 | Sgro |

(56) References Cited

U.S. PATENT DOCUMENTS

| | | |
|---|---|---|
| 7,510,562 B2 | 3/2009 | Lindsay |
| 7,552,853 B2 | 6/2009 | Mas et al. |
| 7,559,937 B2 | 7/2009 | de la Torre et al. |
| 7,572,266 B2 | 8/2009 | Young et al. |
| 7,578,827 B2 | 8/2009 | Gadberry et al. |
| 7,582,095 B2 | 9/2009 | Shipp et al. |
| 7,585,304 B2 | 9/2009 | Hughett |
| 7,615,058 B2 | 11/2009 | Sixto, Jr. et al. |
| 7,615,060 B2 | 11/2009 | Stokes et al. |
| 7,621,926 B2 | 11/2009 | Wixey et al. |
| 7,637,917 B2 | 12/2009 | Whitfield et al. |
| 7,644,848 B2 | 1/2010 | Swayze et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,247 B2 | 6/2010 | Kimura et al. |
| 7,727,248 B2 | 6/2010 | Smith et al. |
| 7,731,724 B2 | 6/2010 | Huitema et al. |
| 7,731,725 B2 | 6/2010 | Gadberry et al. |
| 7,736,388 B2 | 6/2010 | Goldfarb et al. |
| 7,740,639 B2 | 6/2010 | Hummel et al. |
| 7,740,641 B2 | 6/2010 | Huitema |
| 7,744,623 B2 | 6/2010 | Anderson |
| 7,752,853 B2 | 7/2010 | Singh et al. |
| 7,753,250 B2 | 7/2010 | Clauson et al. |
| 7,766,207 B2 | 8/2010 | Mather et al. |
| 7,766,925 B2 | 8/2010 | Stokes et al. |
| 7,770,773 B2 | 8/2010 | Whitman et al. |
| 7,776,058 B2 | 8/2010 | Rosenberg et al. |
| 7,780,688 B2 | 8/2010 | Sakakine et al. |
| 7,793,813 B2 | 9/2010 | Bettuchi |
| 7,806,903 B2 | 10/2010 | Shibata et al. |
| 7,819,886 B2 | 10/2010 | Whitfield et al. |
| 7,823,592 B2 | 11/2010 | Bettuchi et al. |
| 7,857,828 B2 | 12/2010 | Jabba et al. |
| 7,871,416 B2 | 1/2011 | Phillips |
| 7,875,029 B1 | 1/2011 | Hausen |
| 7,887,553 B2 | 2/2011 | Lehman et al. |
| 7,887,554 B2 | 2/2011 | Stokes et al. |
| 7,892,244 B2 | 2/2011 | Monassevitch et al. |
| 7,896,895 B2 | 3/2011 | Boudreaux et al. |
| 7,901,420 B2 | 3/2011 | Dunn |
| 7,905,890 B2 | 3/2011 | Whitfield et al. |
| 7,914,544 B2 | 3/2011 | Nguyen et al. |
| 7,914,551 B2 | 3/2011 | Ortiz et al. |
| 7,942,890 B2 | 5/2011 | D'Agostino et al. |
| 7,947,052 B2 | 5/2011 | Baxter, III et al. |
| 7,954,682 B2 | 6/2011 | Giordano et al. |
| 7,963,433 B2 | 6/2011 | Whitman et al. |
| 7,967,831 B2 | 6/2011 | Rosenberg et al. |
| 7,988,027 B2 | 8/2011 | Olson et al. |
| 7,998,155 B2 | 8/2011 | Manzo |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,048,088 B2 | 11/2011 | Green et al. |
| 8,056,565 B2 | 11/2011 | Zergiebel |
| 8,062,310 B2 | 11/2011 | Shibata et al. |
| 8,062,311 B2 | 11/2011 | Litscher et al. |
| 8,062,314 B2 | 11/2011 | Sixto, Jr. et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,074,857 B2 | 12/2011 | Peterson et al. |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,137,368 B2 | 3/2012 | Kayan et al. |
| 8,142,451 B2 | 3/2012 | Boulnois et al. |
| 8,157,145 B2 | 4/2012 | Shelton, IV et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,177,797 B2 | 5/2012 | Shimoji et al. |
| 8,182,529 B2 | 5/2012 | Gordon et al. |
| 8,187,290 B2 | 5/2012 | Buckman et al. |
| 8,192,449 B2 | 6/2012 | Maier et al. |
| 8,211,119 B2 | 7/2012 | Palmer et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,241,322 B2 | 8/2012 | Whitman et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,287,559 B2 | 10/2012 | Barker et al. |
| 8,308,743 B2 | 11/2012 | Matsuno et al. |
| 8,313,497 B2 | 11/2012 | Walberg et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,138 B2 | 3/2013 | Weisshaupt et al. |
| 8,403,945 B2 | 3/2013 | Whitfield et al. |
| 8,403,946 B2 | 3/2013 | Whitfield et al. |
| 8,408,442 B2 | 4/2013 | Racenet et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,545,519 B2 | 10/2013 | Aguirre et al. |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,716 B2 | 11/2013 | Roskopf et al. |
| 8,585,717 B2 | 11/2013 | Sorrentino et al. |
| 8,603,109 B2 | 12/2013 | Aranyi et al. |
| 8,623,044 B2 | 1/2014 | Timm et al. |
| 8,628,547 B2 | 1/2014 | Weller et al. |
| 8,632,520 B2 | 1/2014 | Otley |
| 8,636,191 B2 | 1/2014 | Meagher |
| 8,652,151 B2 | 2/2014 | Lehman et al. |
| 8,652,152 B2 | 2/2014 | Aranyi et al. |
| 8,663,247 B2 | 3/2014 | Menn et al. |

(56) References Cited

U.S. PATENT DOCUMENTS

| | | |
|---|---|---|
| 8,685,048 B2 | 4/2014 | Adams et al. |
| 8,690,899 B2 | 4/2014 | Kogiso et al. |
| 8,708,210 B2 | 4/2014 | Zemlok et al. |
| 8,708,213 B2 | 4/2014 | Shelton, IV et al. |
| 8,709,027 B2 | 4/2014 | Adams et al. |
| 8,715,299 B2 | 5/2014 | Menn et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,758,392 B2 | 6/2014 | Crainich |
| 8,771,169 B2 | 7/2014 | Whitman et al. |
| 8,795,302 B2 | 8/2014 | Wild |
| 8,808,310 B2 | 8/2014 | Jones et al. |
| 8,814,884 B2 | 8/2014 | Whitfield et al. |
| 8,821,516 B2 | 9/2014 | Huitema |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,900,253 B2 | 12/2014 | Aranyi et al. |
| 8,915,930 B2 | 12/2014 | Huitema et al. |
| 8,915,931 B2 | 12/2014 | Boudreaux et al. |
| 8,939,974 B2 | 1/2015 | Boudreaux et al. |
| 8,945,151 B2 | 2/2015 | Salas |
| 8,950,646 B2 | 2/2015 | Viola |
| 8,968,337 B2 | 3/2015 | Whitfield et al. |
| 8,968,342 B2 | 3/2015 | Wingardner, III et al. |
| 8,973,804 B2 | 3/2015 | Hess et al. |
| 8,986,343 B2 | 3/2015 | Bourque et al. |
| 8,998,935 B2 | 4/2015 | Hart |
| 9,011,464 B2 | 4/2015 | Zammataro |
| 9,011,465 B2 | 4/2015 | Whitfield et al. |
| 9,028,511 B2 | 5/2015 | Weller et al. |
| 9,060,779 B2 | 6/2015 | Martinez |
| 9,084,604 B2 | 7/2015 | Litscher et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel et al. |
| 9,226,825 B2 | 1/2016 | Starksen et al. |
| 9,232,947 B2 | 1/2016 | Brenner et al. |
| 9,265,486 B2 | 2/2016 | Hughett, Sr. et al. |
| 9,271,737 B2 | 3/2016 | Castro et al. |
| 9,282,972 B1 | 3/2016 | Patel et al. |
| 9,282,973 B2 | 3/2016 | Hughett, Sr. et al. |
| 9,358,011 B2 | 6/2016 | Sorrentino et al. |
| 9,364,216 B2 | 6/2016 | Rockrohr et al. |
| 9,364,240 B2 | 6/2016 | Whitfield et al. |
| 9,370,400 B2 | 6/2016 | Parihar |
| 9,393,024 B2 | 7/2016 | Whitfield et al. |
| 9,408,610 B2 | 8/2016 | Hartournbekis |
| 9,414,844 B2 | 8/2016 | Zergiebel et al. |
| 9,433,411 B2 | 9/2016 | Racenet et al. |
| 9,433,422 B2 | 9/2016 | Crainich et al. |
| 9,439,654 B2 | 9/2016 | Sorrentino et al. |
| 9,445,810 B2 | 9/2016 | Cappola |
| 9,445,820 B2 | 9/2016 | Whiting |
| 9,456,824 B2 | 10/2016 | Willett et al. |
| 9,468,444 B2 | 10/2016 | Menn et al. |
| 9,480,477 B2 | 11/2016 | Aranyi et al. |
| 9,480,480 B2 | 11/2016 | Santini et al. |
| 9,486,225 B2 | 11/2016 | Michler et al. |
| 9,498,227 B2 | 11/2016 | Zergiebel et al. |
| 9,504,472 B2 | 11/2016 | Kamler |
| 9,517,064 B2 | 12/2016 | Sarradon |
| 9,526,501 B2 | 12/2016 | Malkowski |
| 9,526,565 B2 | 12/2016 | Strobl |
| 9,532,787 B2 | 1/2017 | Zammataro |
| 9,545,254 B2 | 1/2017 | Sorrentino et al. |
| 9,549,741 B2 | 1/2017 | Zergiebel |
| 9,561,038 B2 | 2/2017 | Shelton, IV et al. |
| 9,566,066 B2 | 2/2017 | Kasvikis |
| 9,597,089 B2 | 3/2017 | Menn |
| 9,642,627 B2 | 5/2017 | Zammataro |
| 9,681,877 B2 | 6/2017 | Blake, III et al. |
| 9,687,247 B2 | 6/2017 | Aranyi et al. |
| 9,700,324 B2 | 7/2017 | Mazzucco et al. |
| 9,717,504 B2 | 8/2017 | Huitema |
| 9,717,505 B2 | 8/2017 | Whitfield et al. |
| 9,724,163 B2 | 8/2017 | Orban |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,763,669 B2 | 9/2017 | Griego |
| 9,775,623 B2 | 10/2017 | Zammataro et al. |
| 9,775,624 B2 | 10/2017 | Rockrohr et al. |
| 9,782,164 B2 | 10/2017 | Mumaw |
| 9,782,181 B2 | 10/2017 | Vitali et al. |
| 9,808,257 B2 | 11/2017 | Armenteros et al. |
| 9,848,886 B2 | 12/2017 | Malkowski et al. |
| 9,855,043 B2 | 1/2018 | Malkowski |
| 9,883,866 B2 | 2/2018 | Roundy et al. |
| 9,931,124 B2 | 4/2018 | Gokharu |
| 9,968,361 B2 | 5/2018 | Aranyi et al. |
| 9,968,362 B2 | 5/2018 | Malkowski et al. |
| 10,004,502 B2 | 6/2018 | Malkowski et al. |
| 10,136,939 B2 | 11/2018 | Minnelli et al. |
| 10,159,484 B2 | 12/2018 | Sorrentino et al. |
| 10,159,491 B2 | 12/2018 | Gokharu |
| 10,159,492 B2 | 12/2018 | Zammataro |
| 10,166,027 B2 | 1/2019 | Aranyi et al. |
| 10,231,732 B1 | 3/2019 | Racenet et al. |
| 10,231,735 B2 | 3/2019 | Sorrentino et al. |
| 10,231,738 B2 | 3/2019 | Sorrentino et al. |
| 10,258,346 B2 | 4/2019 | Zergiebel et al. |
| 10,292,712 B2 | 5/2019 | Shankarsetty |
| 10,349,936 B2 | 7/2019 | Rockrohr et al. |
| 10,349,950 B2 | 7/2019 | Aranyi et al. |
| 10,357,250 B2 | 7/2019 | Lammataro |
| 10,363,045 B2 | 7/2019 | Whitfield et al. |
| 10,368,876 B2 | 8/2019 | Bhatnagar et al. |
| 10,390,831 B2 | 8/2019 | Holsten et al. |
| 10,426,489 B2 | 10/2019 | Baril |
| 2002/0123742 A1 | 9/2002 | Baxter et al. |
| 2003/0014060 A1 | 1/2003 | Wilson et al. |
| 2003/0114867 A1 | 6/2003 | Bolduc et al. |
| 2003/0208231 A1 | 11/2003 | Williamson et al. |
| 2003/0229360 A1 | 12/2003 | Gayton |
| 2004/0097970 A1 | 5/2004 | Hughett |
| 2004/0097971 A1 | 5/2004 | Hughett |
| 2004/0133215 A1 | 7/2004 | Baxter |
| 2004/0138681 A1 | 7/2004 | Pier |
| 2004/0167545 A1 | 8/2004 | Sadler et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0232197 A1 | 11/2004 | Shelton et al. |
| 2005/0010242 A1 | 1/2005 | Lindsay |
| 2005/0090837 A1 | 4/2005 | Sixto et al. |
| 2005/0096670 A1 | 5/2005 | Wellman et al. |
| 2005/0096671 A1 | 5/2005 | Wellman et al. |
| 2005/0107810 A1 | 5/2005 | Morales et al. |
| 2005/0107811 A1 | 5/2005 | Starksen et al. |
| 2005/0107871 A1 | 5/2005 | Realyvasquez et al. |
| 2005/0125010 A1 | 6/2005 | Smith et al. |
| 2005/0149068 A1 | 7/2005 | Williams et al. |
| 2005/0149069 A1 | 7/2005 | Bertolero et al. |
| 2005/0171560 A1 | 8/2005 | Hughett |
| 2005/0175703 A1 | 8/2005 | Hunter et al. |
| 2005/0177176 A1 | 8/2005 | Gerbi et al. |
| 2005/0216036 A1 | 9/2005 | Nakao |
| 2005/0216056 A1 | 9/2005 | Valdevit et al. |
| 2005/0222665 A1 | 10/2005 | Aranyi |
| 2005/0228416 A1 | 10/2005 | Burbank et al. |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277956 A1 | 12/2005 | Francese et al. |
| 2005/0277958 A1 | 12/2005 | Levinson |

(56) References Cited

U.S. PATENT DOCUMENTS

| | | |
|---|---|---|
| 2005/0288689 A1 | 12/2005 | Kammerer et al. |
| 2006/0000867 A1 | 1/2006 | Shelton et al. |
| 2006/0004388 A1 | 1/2006 | Whayne et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020271 A1 | 1/2006 | Stewart et al. |
| 2006/0079115 A1 | 4/2006 | Aranyi |
| 2006/0085015 A1 | 4/2006 | Whitfield et al. |
| 2006/0085021 A1 | 4/2006 | Wenzler |
| 2006/0100649 A1 | 5/2006 | Hart |
| 2006/0124485 A1 | 6/2006 | Kennedy |
| 2006/0163312 A1 | 7/2006 | Viola et al. |
| 2006/0173470 A1 | 8/2006 | Oray et al. |
| 2006/0190013 A1 | 8/2006 | Menn |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235439 A1 | 10/2006 | Molitor et al. |
| 2006/0241655 A1 | 10/2006 | Viola |
| 2006/0259045 A1 | 11/2006 | Damarati |
| 2006/0259049 A1 | 11/2006 | Harada et al. |
| 2007/0021766 A1 | 1/2007 | Belagali et al. |
| 2007/0038233 A1 | 2/2007 | Martinez et al. |
| 2007/0049947 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0083218 A1 | 4/2007 | Morris |
| 2007/0093790 A1 | 4/2007 | Downey et al. |
| 2007/0112365 A1 | 5/2007 | Hilal et al. |
| 2007/0118161 A1 | 5/2007 | Kennedy et al. |
| 2007/0118174 A1 | 5/2007 | Chu |
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |
| 2007/0203510 A1 | 8/2007 | Bettuchi |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0004636 A1 | 1/2008 | Walberg et al. |
| 2008/0045981 A1 | 2/2008 | Margolin et al. |
| 2008/0051808 A1 | 2/2008 | Rivera et al. |
| 2008/0103510 A1 | 5/2008 | Taylor et al. |
| 2008/0147092 A1 | 6/2008 | Rogge et al. |
| 2008/0167665 A1 | 7/2008 | Arp et al. |
| 2008/0228199 A1 | 9/2008 | Cropper et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312670 A1 | 12/2008 | Lutze et al. |
| 2009/0088783 A1 | 4/2009 | Kennedy et al. |
| 2009/0182193 A1 | 7/2009 | Whitman et al. |
| 2009/0204115 A1 | 8/2009 | Dees, Jr. et al. |
| 2009/0209946 A1 | 8/2009 | Swayze et al. |
| 2009/0228023 A1 | 9/2009 | Cui |
| 2009/0261142 A1 | 10/2009 | Milliman et al. |
| 2009/0264904 A1 | 10/2009 | Aldrich et al. |
| 2009/0312775 A1 | 12/2009 | Gilkey et al. |
| 2009/0326558 A1 | 12/2009 | Cui et al. |
| 2010/0089970 A1 | 4/2010 | Smith et al. |
| 2010/0274264 A1 | 10/2010 | Schulz et al. |
| 2010/0318103 A1 | 12/2010 | Cheng et al. |
| 2010/0331862 A1 | 12/2010 | Monassevitch et al. |
| 2011/0054498 A1 | 3/2011 | Monassevitch et al. |
| 2011/0087218 A1* | 4/2011 | Boudreaux ........ A61B 18/1445 606/41 |
| 2011/0087220 A1 | 4/2011 | Felder et al. |
| 2011/0087268 A1 | 4/2011 | Livneh |
| 2011/0144662 A1 | 6/2011 | McLawhorn et al. |
| 2011/0208211 A1 | 8/2011 | Whitfield et al. |
| 2011/0208212 A1 | 8/2011 | Zergiebel et al. |
| 2011/0218554 A1 | 9/2011 | Cheng et al. |
| 2011/0224700 A1 | 9/2011 | Schmidt et al. |
| 2011/0276049 A1* | 11/2011 | Gerhardt ............ A61B 18/1402 606/45 |
| 2011/0295290 A1 | 12/2011 | Whitfield |
| 2011/0313437 A1 | 12/2011 | Yeh |
| 2012/0022526 A1 | 1/2012 | Aldridge et al. |
| 2012/0046671 A1 | 2/2012 | Matsuoka et al. |
| 2012/0048759 A1 | 3/2012 | Disch et al. |
| 2012/0053402 A1 | 3/2012 | Conlon et al. |
| 2012/0226291 A1 | 9/2012 | Malizia et al. |
| 2012/0253298 A1 | 10/2012 | Henderson et al. |
| 2012/0265220 A1 | 10/2012 | Menn |
| 2012/0330326 A1 | 12/2012 | Creston et al. |
| 2013/0041379 A1 | 2/2013 | Bodor et al. |
| 2013/0131697 A1 | 5/2013 | Hartoumbekis |
| 2013/0165951 A1 | 6/2013 | Blake, III |
| 2013/0172909 A1 | 7/2013 | Harris |
| 2013/0172910 A1 | 7/2013 | Malkowski |
| 2013/0175320 A1 | 7/2013 | Mandakolathur Vasudevan et al. |
| 2013/0226200 A1 | 8/2013 | Kappel et al. |
| 2013/0253540 A1 | 9/2013 | Castro et al. |
| 2013/0325057 A1 | 12/2013 | Larson et al. |
| 2014/0074143 A1 | 3/2014 | Fitzgerald et al. |
| 2014/0188159 A1 | 7/2014 | Steege |
| 2014/0263565 A1 | 9/2014 | Lytle, IV et al. |
| 2014/0276970 A1 | 9/2014 | Messerly et al. |
| 2014/0371728 A1 | 12/2014 | Vaughn |
| 2015/0032131 A1 | 1/2015 | Sorrentino et al. |
| 2015/0201953 A1 | 7/2015 | Strobl et al. |
| 2015/0265282 A1 | 9/2015 | Miles et al. |
| 2015/0313452 A1 | 11/2015 | Nasser et al. |
| 2015/0314451 A1 | 11/2015 | Nixon |
| 2016/0004956 A1 | 1/2016 | Reynolds et al. |
| 2016/0030044 A1 | 2/2016 | Zammataro |
| 2016/0113655 A1 | 4/2016 | Holsten |
| 2016/0151071 A1 | 6/2016 | Tokarz et al. |
| 2016/0213377 A1 | 7/2016 | Shankarsetty |
| 2016/0242767 A1 | 8/2016 | Kasvikis |
| 2016/0242789 A1 | 8/2016 | Sorrentino et al. |
| 2016/0256157 A1 | 9/2016 | Rockrohr et al. |
| 2016/0256158 A1 | 9/2016 | Whitfield et al. |
| 2016/0262764 A1 | 9/2016 | Gokharu |
| 2016/0296236 A1 | 10/2016 | Whitfield et al. |
| 2016/0338695 A1 | 11/2016 | Hartoumbekis |
| 2016/0338699 A1 | 11/2016 | Sorrentino et al. |
| 2017/0027581 A1 | 2/2017 | Zergiebel et al. |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0172780 A1 | 6/2017 | Murthy Aravalli |
| 2017/0202567 A1 | 7/2017 | Griffiths et al. |
| 2017/0238936 A1 | 8/2017 | Mujawar |
| 2017/0245921 A1 | 8/2017 | Joseph et al. |
| 2017/0252042 A1 | 9/2017 | Kethman et al. |
| 2017/0258472 A1 | 9/2017 | Aranyi et al. |
| 2017/0290587 A1 | 10/2017 | Schober et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0021041 A1 | 1/2018 | Zhang et al. |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |

(56) References Cited

U.S. PATENT DOCUMENTS

| | | |
|---|---|---|
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |
| 2019/0021738 A1 | 1/2019 | Hartoumbekis |
| 2019/0038375 A1 | 2/2019 | Baril et al. |
| 2019/0046202 A1 | 2/2019 | Baril et al. |
| 2019/0046203 A1 | 2/2019 | Baril et al. |
| 2019/0046207 A1 | 2/2019 | Czernik et al. |
| 2019/0046208 A1 | 2/2019 | Baril et al. |
| 2019/0053806 A1 | 2/2019 | Zhang et al. |
| 2019/0053808 A1 | 2/2019 | Baril et al. |
| 2019/0059904 A1 | 2/2019 | Zammataro |
| 2019/0076147 A1 | 3/2019 | Baril et al. |
| 2019/0076148 A1 | 3/2019 | Baril et al. |
| 2019/0076149 A1 | 3/2019 | Baril et al. |
| 2019/0076150 A1 | 3/2019 | Gokharu |
| 2019/0076210 A1 | 3/2019 | Baril et al. |
| 2019/0133583 A1 | 5/2019 | Baril et al. |
| 2019/0133584 A1 | 5/2019 | Baril et al. |
| 2019/0133593 A1 | 5/2019 | P V R |
| 2019/0133594 A1 | 5/2019 | Dinino et al. |
| 2019/0133595 A1 | 5/2019 | Baril et al. |
| 2019/0150935 A1 | 5/2019 | Raikar et al. |
| 2019/0175176 A1 | 6/2019 | Zammataro |
| 2019/0175187 A1 | 6/2019 | P V R |
| 2019/0175188 A1 | 6/2019 | P V R |
| 2019/0175189 A1 | 6/2019 | P V R |
| 2019/0192139 A1 | 6/2019 | Rockrohr et al. |
| 2019/0209177 A1 | 7/2019 | Whitfield et al. |
| 2019/0216464 A1 | 7/2019 | Baril et al. |
| 2019/0239893 A1 | 8/2019 | Shankarsetty |

FOREIGN PATENT DOCUMENTS

| | | |
|---|---|---|
| CN | 103251441 A | 8/2013 |
| CN | 104605911 B | 2/2017 |
| DE | 202005001664 U1 | 5/2005 |
| DE | 202007003398 U1 | 6/2007 |
| DE | 202009006113 U1 | 7/2009 |
| EP | 0000756 A1 | 2/1979 |
| EP | 0406724 A1 | 1/1991 |
| EP | 0514139 A2 | 11/1992 |
| EP | 0732078 A2 | 9/1996 |
| EP | 1611856 A1 | 1/2006 |
| EP | 1769757 A1 | 4/2007 |
| EP | 3132756 A1 | 2/2017 |
| GB | 2073022 A | 10/1981 |
| JP | 2003033361 A | 2/2003 |
| JP | 2006154230 A | 6/2006 |
| JP | 2006277221 A | 10/2006 |
| JP | 2008017876 A | 1/2008 |
| JP | 2011186812 A | 9/2011 |
| JP | 2013166982 A | 8/2013 |
| WO | 9003763 A1 | 4/1990 |
| WO | 0042922 A1 | 7/2000 |
| WO | 0166001 A2 | 9/2001 |
| WO | 0167965 A1 | 9/2001 |
| WO | 2016192096 A1 | 12/2016 |
| WO | 2016192718 A2 | 12/2016 |
| WO | 2016197350 A1 | 12/2016 |
| WO | 2016206015 A1 | 12/2016 |
| WO | 2017084000 A1 | 5/2017 |
| WO | 2017146138 A1 | 8/2017 |

OTHER PUBLICATIONS

Extended European Search Report corresponding to Patent Application EP 18155158.1 dated Jun. 28, 2018.
Extended European Search Report corresponding to Patent Application EP 15877428.1 dated Jul. 2, 2018.
Extended European Search Report corresponding to Patent Application EP 18157789.1 dated Jul. 5, 2018.
Canadian Office Action corresponding to Patent Application CA 2,972,444 dated Aug. 9, 2018.
Extended European Search Report corresponding to Patent Application EP 18156458.4 dated Sep. 3, 2018.
Extended European Search Report corresponding to Patent Application EP 18171682.0 dated Sep. 18, 2018.
Extended European Search Report corresponding to Patent Application EP 15878354.8 dated Sep. 19, 2018.
Extended European Search Report corresponding to Patent Application EP 18183394.8 dated Sep. 28, 2018.
Extended European Search Report corresponding to Patent Application EP 18163041.9 dated Sep. 28, 2018.
Extended European Search Report corresponding to Patent Application EP 18170524.5 dated Oct. 1, 2018.
Japanese Office Action corresponding to Patent Application JP 2017-536546 dated Oct. 15, 2018.
Extended European Search Report corresponding to Patent Application EP 18187640.0 dated Nov. 30, 2018.
Chinese First Office Action corresponding to Patent Application CN 201510696298.9 dated Dec. 3, 2018.
Extended European Search Report corresponding to Patent Application EP 18158143.0 dated Dec. 5, 2018.
International Search Report corresponding to Int'l Patent Appln. PCT/US2018/050316 dated Dec. 31, 2018.
International Search Report corresponding to Int'l Patent Appln. PCT/US2018/050336 dated Jan. 7, 2019.
International Search Report corresponding to Int'l Patent Appln. PCT/US2018/050325 dated Jan. 7, 2019.
International Search Report corresponding to Int'l Patent Appln. PCT/US2018/045306 dated Jan. 16, 2019.
International Search Report corresponding to Int'l Patent Appln. PCT/US2018/050349 dated Jan. 21, 2019.
International Search Report corresponding to Int'l Patent Appln. PCT/US2018/045725 dated Jan. 28, 2019.
Extended European Search Report corresponding to European Patent Application EP 18208630.6 dated Feb. 12, 2019.
International Search Report corresponding to Int'l Patent Appln. PCT/US2018/057910 dated Feb. 22, 2019.
International Search Report corresponding to Int'l Patent Appln. PCT/US2018/057922 dated Feb. 22, 2019.
International Search Report corresponding to Int'l Patent Appln. PCT/US2018/058078 dated Feb. 22, 2019.
International Search Report corresponding to Int'l Patent Appln. PCT/US2018/058603 dated Feb. 22, 2019.
International Search Report corresponding to Int'l Patent Appln. PCT/US2018/057221 dated Mar. 11, 2019.
Extended European Search Report corresponding to European Patent Application EP 18212043.6 dated Apr. 24, 2019.
Extended European Search Report corresponding to European Patent Application EP 18211565.9 dated Apr. 26, 2019.
Extended European Search Report corresponding to European Patent Application EP 18211921.4 dated Apr. 30, 2019.
Chinese First Office Action corresponding to Chinese Patent Application CN 201510868226.8 dated May 29, 2019.
Extended European Search Report corresponding to European Patent Application EP 15905685.2 dated May 29, 2019.
European Office Action corresponding to European Patent Application EP 17157606.9 dated Jul. 2, 2019.
Extended European Search Report corresponding to European Patent Application EP 15908025.8 dated Jul. 2, 2019.
Extended European Search Report corresponding to European Patent Application EP 18212054.3 dated Jul. 3, 2019.
Partial Supplementary European Search Report corresponding to European Patent Application EP 16884297.9 dated Jul. 30, 2019.
Extended European Search Report issued in EP application No. 18187690.5 dated Nov. 30, 2018, 10 pages.

(56) References Cited

OTHER PUBLICATIONS

"Salute II Disposable Fixation Device", Technique Guide—Laparoscopic and Open Inguinal and Ventral Hernia Repair; Davol, A Bard Company, 2006; (7 Pages).
First European Examination Report issued in corresponding European Application No. 18187690.5 dated Mar. 23, 2020, 8 pages.

* cited by examiner

GEARED ACTUATION MECHANISM AND SURGICAL CLIP APPLIER INCLUDING THE SAME

CROSS-REFERENCE TO RELATED APPLICATIONS

This application claims the benefit of and priority to U.S. Provisional Patent Application No. 62/542,335 filed Aug. 8, 2017, the entire disclosure of which is incorporated by reference herein.

BACKGROUND

Technical Field

The present disclosure relates to surgical clip appliers. More particularly, the present disclosure relates to geared actuation mechanisms for surgical clip appliers and surgical clip appliers including the same.

Description of Related Art

Surgical clip appliers are known in the art and are used for a number of distinct and useful surgical procedures. In the case of a laparoscopic surgical procedure, access to the interior of an abdomen is achieved through narrow tubes or cannulas inserted through a small entrance incision in the skin. Minimally invasive procedures performed elsewhere in the body are often generally referred to as endoscopic procedures.

Endoscopic surgical clip appliers having various sizes (e.g., diameters), that are configured to apply a variety of diverse surgical clips, are also known in the art, and are capable of applying a single or multiple surgical clips during an entry to the body cavity. Such surgical clips are typically fabricated from a biocompatible material and are usually compressed over tissue. Once applied to tissue, the compressed surgical clip terminates the flow of fluid therethrough.

SUMMARY

As detailed herein and shown in the drawing figures, as is traditional when referring to relative positioning on a surgical instrument, the term "proximal" refers to the end of the apparatus or component thereof which is closer to the user and the term "distal" refers to the end of the apparatus or component thereof which is further away from the user. Further, to the extent consistent, any or all of the aspects and features detailed herein may be used in conjunction with any or all of the other aspects and features detailed herein.

Provided in accordance with an aspect of the present disclosure is an actuation mechanism for a surgical clip applier including a drive bar movable through a stroke having a first stroke portion and a second stroke portion to fire at least one surgical clip. The drive bar includes an output gear rack associated therewith. A trigger is pivotable from an un-actuated position to an actuated position. A first intermediate gear includes an input portion and an output portion. The input portion of the first intermediate gear is operably coupled to the trigger such that pivoting of the trigger from the un-actuated position to the actuated position rotates the first intermediate gear. A second intermediate gear includes an input portion and an output portion. The output portions of the first and second intermediate gears define different diameters. The input portion of the second intermediate gear is operably coupled to the trigger such that pivoting of the trigger from the un-actuated position to the actuated position rotates the second intermediate gear. In the first portion of the stroke length, the output portion of the first intermediate gear is disposed in meshed engagement with the gear rack and the output portion of the second intermediate gear is disengaged from the gear rack such that the first intermediate gear drives the drive bar along the first portion of the stroke length in response to pivoting of the trigger. In the second portion of the stroke length, the output portion of the second intermediate gear is disposed in meshed engagement with the gear rack and the output portion of the first intermediate gear is disengaged from the gear rack such that the second intermediate gear drives the drive bar along the second portion of the stroke length in response to pivoting of the trigger. A different mechanical advantage is provided in the first portion of the stroke length as compared to the second portion of the stroke length.

In an aspect of the present disclosure, the mechanical advantage provided in the first portion of the stroke length is less than the mechanical advantage provided in the second portion of the stroke length.

In another aspect of the present disclosure, the first portion of the stroke length is greater than the second portion of the stroke length.

In yet another aspect of the present disclosure, the trigger is pivotable through an input rotation from the un-actuated position to the actuated position. The input rotation includes a first portion corresponding to the first portion of the stroke length and a second portion corresponding to the second portion of the stroke length. In such aspects, the first portion of the input rotation may be less than the second portion of the input rotation and/or the first portion of the stroke length may be greater than the second portion of the stroke length.

In still another aspect of the present disclosure, an input gear is associated with the trigger and a transmission gear including an input portion and an output portion is disposed between the input gear and the first and second intermediate gears. The input portion of the transmission gear is disposed in meshed engagement with the input gear and the output portion of the transmission gear disposed in meshed engagement with the input portions of the first and second intermediate gears.

A handle assembly of a surgical clip applier provided in accordance with aspects of the present disclosure includes a housing defining a body portion and a fixed handle portion extending from the body portion and an actuation mechanism such as the actuation mechanism according to any of the above-noted aspects or any of the other aspects detailed herein.

In aspects, the housing is configured to receive an elongated assembly supporting an end effector assembly at a distal end portion thereof. The drive bar is configured to operably interface with an actuation member of the elongated assembly.

A surgical clip applier provided in accordance with aspects of the present disclosure includes a handle assembly and an elongated assembly extending distally from the handle assembly and supporting an end effector assembly at a distal end portion thereof. The elongated assembly includes an actuation member movable to fire at least one surgical clip from the end effector assembly. The handle assembly includes a housing defining a body portion and a fixed handle portion extending from the body portion. The handle assembly further includes an actuation mechanism such as the actuation mechanism according to any of the above-noted aspects or any of the other aspects detailed herein.

In aspects, the elongated assembly is releasably engagable with the handle assembly.

BRIEF DESCRIPTION OF THE DRAWINGS

Aspects and features of the presently-disclosed geared actuation mechanisms for surgical clip appliers and clip surgical clip appliers including the same are described in detail with reference to the drawing figures wherein like reference numerals identify similar or identical structural elements and.

DETAILED DESCRIPTION

The present disclosure provides geared actuation mechanisms for surgical clip appliers and surgical clip appliers including the same.

Figure 1:
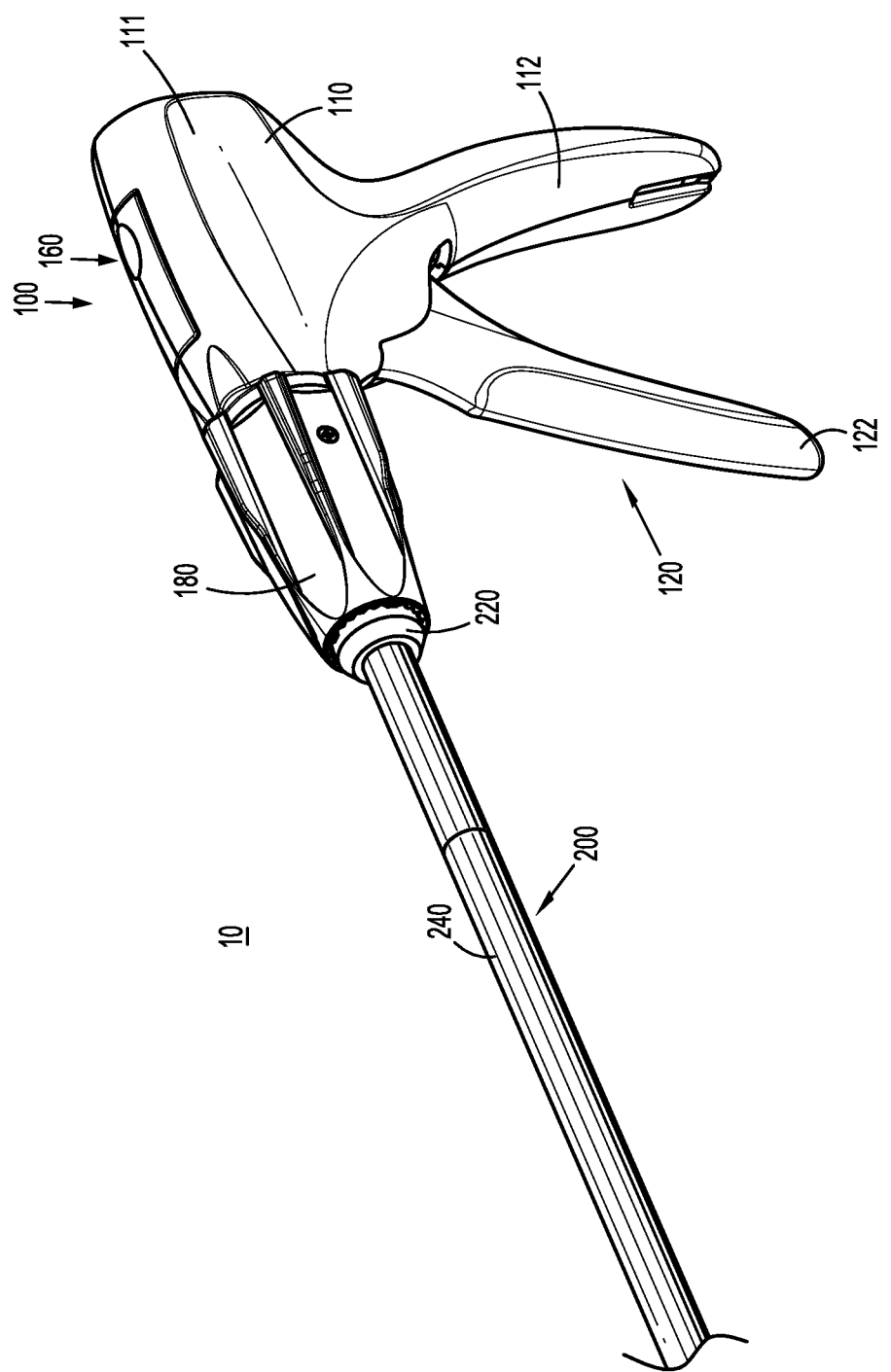
FIG. 1 is a front, perspective view of a surgical clip applier provided in accordance with the present disclosure including a handle assembly having an elongated assembly engaged therewith.
Figure 2:
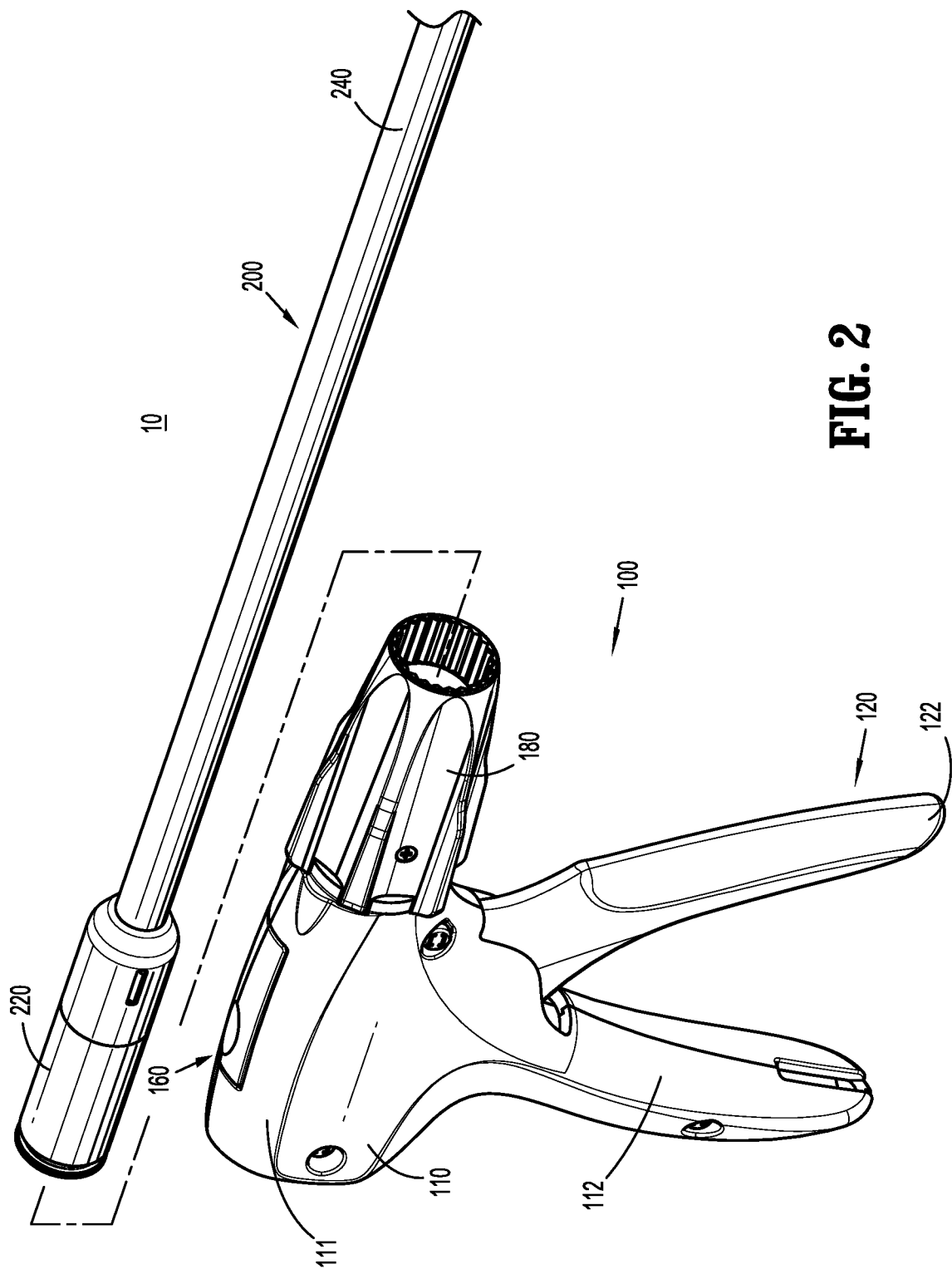
FIG. 2 is front, perspective view of the surgical clip applier of FIG. 1 with the elongated assembly removed from the handle assembly.

Turning to FIGS. 1-2, a surgical clip applier embodying the aspects and features of the present disclosure is shown generally identified by reference numeral 10. Surgical clip applier 10 generally includes a handle assembly 100 and a plurality of elongated assemblies 200, 300 (FIG. 4) selectively connectable to handle assembly 100. Handle assembly 100 is configured to operate each of the plurality of elongated assemblies 200, 300 (FIG. 4) upon connection thereto, and may be configured as a sterilizable, reusable component such that handle assembly 100 may be repeatedly used with different and/or additional elongated assemblies 200, 300 (FIG. 4) during the course of one or more surgical procedures. The elongated assemblies 200, 300 (FIG. 4) may be configured as single-use disposable components, limited-use disposable components, or reusable components, depending upon a particular purpose and/or the configuration of the particular elongated assembly. In either configuration, the need for multiple handle assemblies 100 is obviated and, instead, the surgeon need only select an appropriate elongated assembly 200, 300 (FIG. 4) and connect that elongated assembly to handle assembly 100 in preparation for use.

Handle assembly 100 generally includes a housing 110, an actuation mechanism 120 operably associated with housing 110, a latch assembly 160 operably associated with housing 110, a rotating receiver assembly 180 operably coupled to a distal portion of housing 110, and, in embodiments, a ratchet mechanism (not shown) operably disposed within housing 110. Housing 110 supports and/or encloses the operating components of handle assembly 100 and is detailed below. Actuation mechanism 120 is configured to enable selective firing of one or more surgical clips (not shown) from the end effector of the attached elongated assembly, as also detailed below.

Latch assembly 160 is configured to facilitate releasable locking engagement of the elongated assembly with handle assembly 100. Rotating receiver assembly 180 is configured to receive a proximal end portion of the elongated assembly and to enable selective rotation thereof relative to housing 110. The ratchet mechanism is configured to enable ratcheting actuation of actuation mechanism 120, when an elongated assembly configured for ratcheting actuation is connected to handle assembly 100. Details of latch assembly 160, rotating receiver assembly 180, and the ratchet mechanism can be found in International Application No. PCT/CN2016/096666, filed on Aug. 26, 2016, the entire contents of which is hereby incorporated herein by reference. Alternatively or additionally, latch assembly 160, rotating receiver assembly 180, and/or the ratchet mechanism may be configured as detailed in International Application No. PCT/CN2016/071178, filed on Jan. 18, 2016, the entire contents of which is also hereby incorporated herein by reference.

Figure 3:
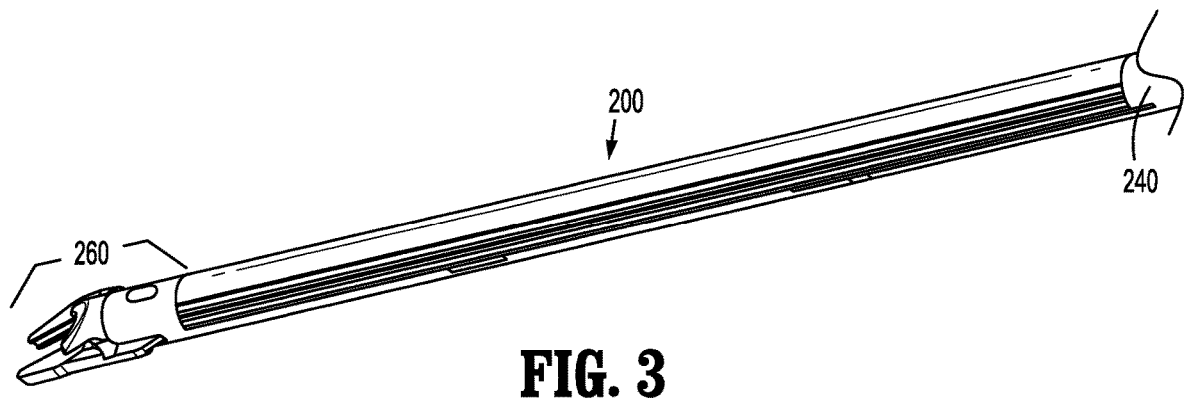
FIG. 3 is a side, perspective view of a distal end portion of the elongated assembly of FIGS. 1 and 2.
Figure 4:
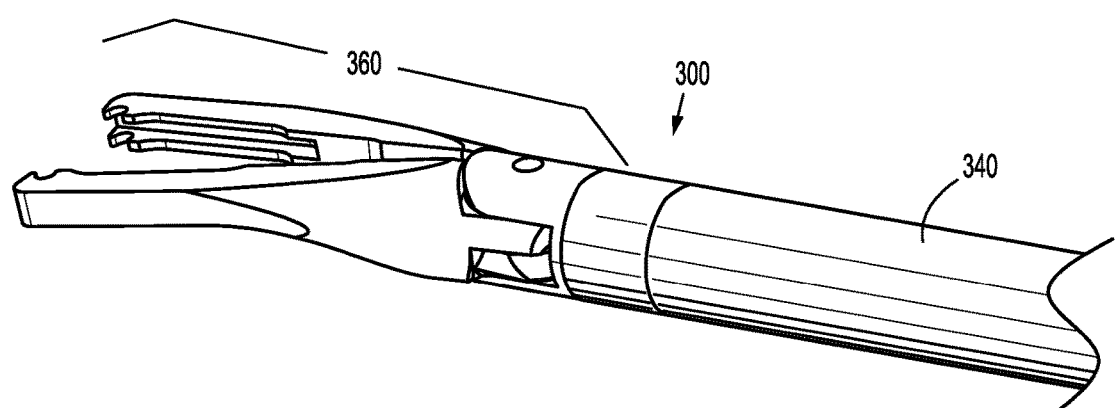
FIG. 4 is a side, perspective view of a distal end portion of another elongated assembly configured for use with the surgical clip applier of FIG. 1.

With additional reference to FIGS. 3 and 4, as noted above, handle assembly 100 is configured for use with different elongated assemblies such as, for example, elongated assembly 200 (FIGS. 1-3) and elongated assembly 300 (FIG. 4). Handle assembly 100, more specifically, is configured for both ratcheting use, e.g., in connection with elongated assembly 200 (FIGS. 1-3), and non-ratcheting use, e.g., in connection with elongated assembly 300 (FIG. 4). Elongated assemblies 200, 300 are described briefly below. A more detailed discussion of elongated assemblies, e.g., elongated assemblies 200, 300, configured for use with handle assembly 100 can be found in International Application Nos. PCT/CN2016/096666 and/or PCT/CN2016/071178, previously incorporated by reference herein in their entireties, and additionally or alternatively as in International Application No. PCT/CN2015/091603, filed on Oct. 10, 2015, the entire contents of which is likewise hereby incorporated herein by reference.

Referring to FIGS. 1-3, elongated assembly 200 is configured for ratcheting use and generally includes a proximal hub 220, an elongated shaft 240 extending distally from proximal hub 220, an end effector assembly 260 disposed towards a distal end portion of elongated shaft 240, and an inner drive assembly (not shown) operably coupled between handle assembly 100 and end effector assembly 260 when elongated assembly 200 is engaged with handle assembly 100 to enable the sequential firing of at least one surgical clip (not shown) about tissue. End effector assembly 260 of elongated assembly 200 may be configured to fire surgical clips similar to those shown and described in U.S. Pat. No. 7,819,886 or 7,905,890, the entire contents of each of which is hereby incorporated herein by reference.

Referring to FIG. 4, elongated assembly 300 is configured for non-ratcheting use and generally includes a proximal hub (not shown), an elongated shaft 340 extending distally from the proximal hub, an end effector assembly 360 disposed towards a distal end portion of elongated shaft 340, and an inner drive assembly (not shown) operably coupled between handle assembly 100 and end effector assembly 360 when elongated assembly 300 is engaged with handle assembly 100 to enable grasping and/or manipulation of tissue, retrieval of a surgical clip, and firing of the surgical clip about tissue. It is contemplated that end effector assembly 360 of elongated assembly 300 may be configured to fire surgical clips similar to those shown and described in U.S.

Pat. No. 4,834,096, the entire contents of which is hereby incorporated herein by reference.

Referring generally to FIGS. 1-4, although exemplary elongated assemblies 200, 300 configured for ratcheting and non-ratcheting use, respectively, are detailed above, it is contemplated that various other elongated assemblies for performing various different surgical tasks and/or having various different configurations suitable for ratcheting or non-ratcheting use may likewise be utilized with handle assembly 100.

Figure 5:
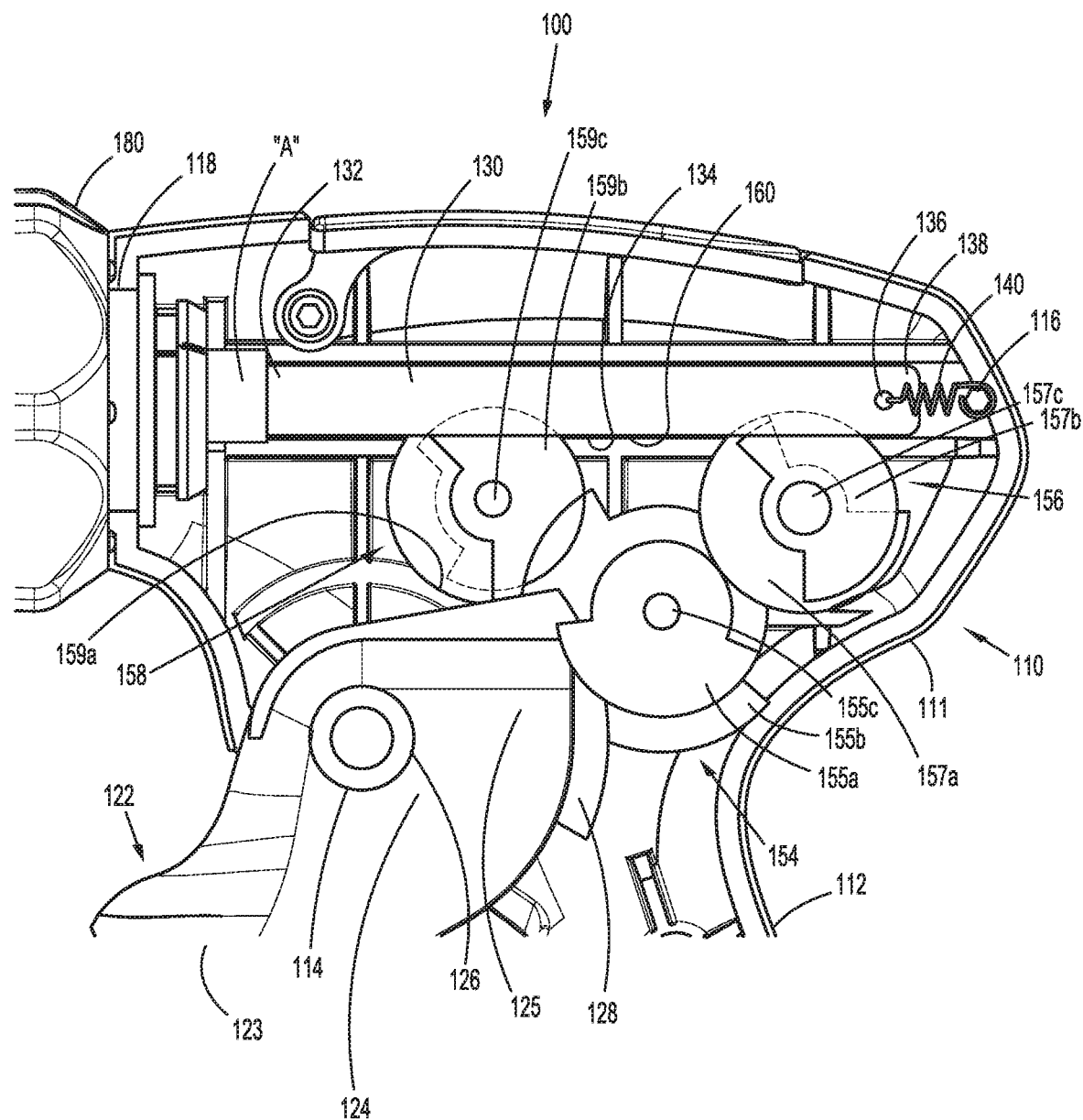
FIG. 5 is an enlarged, longitudinal, cross-sectional view of a portion of the handle assembly of the surgical clip applier of FIG. 1.

Turning to FIGS. 1, 2, and 5, housing 110 of handle assembly 100 defines a body portion 111 and a fixed handle portion 112 depending from body portion 111. Body portion 111 of housing 110 includes an internal pivot post 114 extending transversely within body portion 111, a retention post 116 disposed towards a proximal end of body portion 111 and likewise extending transversely within body portion 111, and a distal opening 118 through which a proximal end portion of an actuation member "A" of an elongated assembly, e.g., elongated assembly 200 (FIGS. 1-3) or elongated assembly 300 (FIG. 4), extends when the elongated assembly is engaged with handle assembly 100.

Actuation mechanism 120 is operably supported by housing 110 and includes a trigger 122, a drive bar 130, a biasing member 140, and a gear assembly 150. Trigger 122 includes a grasping portion 123, an intermediate pivot portion 124, and a proximal extension 125. Grasping portion 123 of trigger 122 extends downwardly from body portion 111 of housing 110 in opposed relation relative to fixed handle portion 112 of housing 110. Grasping portion 123 is configured to facilitate grasping and manipulation of trigger 122. Intermediate pivot portion 124 of trigger 122 is at least partially disposed within housing 110 and defines a pivot aperture 126 that is configured to receive pivot post 114 of housing 110 so as to enable pivoting of trigger 122 about pivot post 114 and relative to housing 110, e.g., between an un-actuated position, wherein grasping portion 123 of trigger 122 is spaced-apart relative to fixed handle portion 112, and an actuated position, wherein grasping portion 123 of trigger 122 is approximated relative to fixed handle portion 112.

Proximal extension 125 of trigger 122 is disposed on an opposite side of intermediate pivot portion 124 and, thus, pivot post 114, as compared to grasping portion 123 of trigger 122. As such, pivoting of grasping portion 123 to rotate in one direction, e.g., proximally towards fixed handle portion 112, pivots proximal extension 125 to rotate in the opposite direction, e.g., distally. Proximal extension 125 of trigger 122 defines an arcuate gear portion 128 that functions as an input gear 152 of gear assembly 150, as detailed below.

The actuation member "A" of the elongated assembly engaged with handle assembly 100 is selectively translatable in response to actuation of actuation mechanism 120 to fire a surgical clip (not shown) supported at the end effector assembly of the elongated assembly about tissue. More specifically, drive bar 130 is slidably disposed within body portion 111 of housing 110 in longitudinal alignment with the actuation member "A" such that distal sliding of drive bar 130 through body portion 111 of housing urges a distal end portion 132 of drive bar 130 into contact with actuation member "A" to thereby translate actuation member "A" distally, e.g., to fire a surgical clip supported at the end effector assembly of the elongated assembly.

Figure 6:
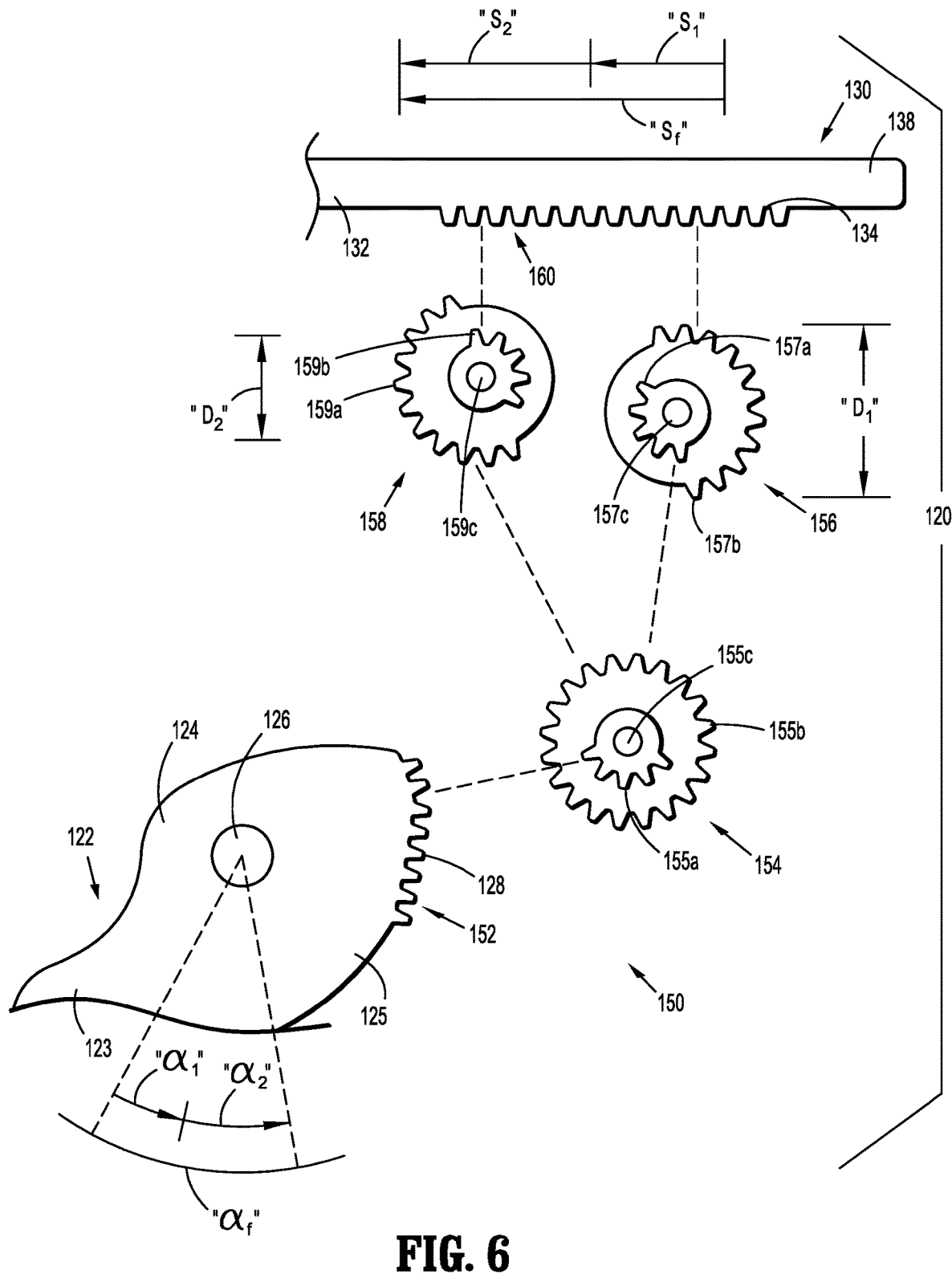
FIG. 6 is an exploded, side view of an actuation mechanism of the handle assembly of the surgical clip applier of FIG. 1.

With additional reference to FIG. 6, drive bar 130 defines a linear gear rack 134 extending along at least a portion of an underside surface thereof. Linear gear rack 134 functions as an output gear 160 of gear assembly 150, as detailed below. Drive bar 130, as detailed above, is slidable through body portion 111 of housing to urge distal end portion 132 of drive bar 130 into actuation member "A" to translate actuation member "A" distally to thereby to fire a surgical clip supported at the end effector assembly of the elongated assembly. Drive bar 130, more specifically, is slidable from an un-actuated, proximal position to an actuated, distal position in order to fire a surgical clip supported at the end effector assembly of the elongated assembly. Biasing member 140 is engaged at a first, proximal end portion thereof to retention post 116 of body portion 111 of housing 110 and at a second, distal end portion thereof through an aperture 136 defined through a proximal end portion 138 of drive bar 130. In this manner, biasing member 140 biases drive bar 130 towards the un-actuated, proximal position.

Gear assembly 150 includes, as noted above, an input gear 152 (defined by arcuate gear portion 128 of proximal extension 125 of trigger 122) and an output gear 160 (defined by linear gear rack 134 of drive bar 130). Gear assembly 150 further includes a transmission gear 154, a first intermediate gear 156, and a second intermediate gear 158.

Transmission gear 154 is configured as a compound gear including an arcuate input gear portion 155a (extending a partial or full circumference) and an arcuate output gear portion 155b (extending a partial or full circumference). Arcuate input gear portion 155a of transmission gear 154 is disposed in meshed engagement with input gear 152, e.g., arcuate gear portion 128 of proximal extension 125 of trigger 122. Transmission gear 154 is rotatably mounted about a pin 155c that is fixed relative to and extends transversely through body portion 111 of housing 110. In embodiments, arcuate input gear portion 155a defines an arc having a diameter different from a diameter of the arc defined by arcuate output gear portion 155b. In embodiments, the diameter of arcuate input gear portion 155a is smaller than the diameter of arcuate output gear portion 155b, although other configurations are also contemplated.

First and second intermediate gears 156, 158, respectively, similar to transmission gear 154, are configured as compound gears each including a respective arcuate input gear portion 157a, 159a (extending a partial or full circumference) and a respective arcuate output gear portion 157b, 159b (extending a partial or full circumference). Arcuate input gear portions 157a, 159a of first and second intermediate gears 156, 158, respectively, are disposed in meshed engagement with arcuate output gear portion 155b of transmission gear 154. More specifically, first intermediate gear 156 is positioned proximally adjacent transmission gear 154 such that arcuate input gear portion 157a thereof is disposed in meshed engagement with arcuate output gear portion 155b of transmission gear 154, and second intermediate gear 158 is positioned distally adjacent transmission gear 154 such that arcuate input gear portion 159a thereof is disposed in meshed engagement with arcuate output gear portion 155b of transmission gear 154, although other configurations are also contemplated. First and second intermediate gears 156, 158 are rotatably mounted about pins 157c, 159c, respectively, that are fixed relative to and extend transversely through body portion 111 of housing 110.

Arcuate output gear portion 157b of first intermediate gear 156 is configured to be disposed in meshed engagement with output gear 160, e.g., linear gear rack 134 of drive bar 130, during a first portion "$S_1$" of the full output stroke length "$S_f$" of drive bar 130. However, once drive bar 130 is moved distally along the full output stroke length "$S_f$" beyond the first portion "$S_1$" to a second portion "$S_2$"

thereof, linear gear rack 134 is moved distally of and out of engagement with arcuate output gear portion 157b of first intermediate gear 156.

Arcuate output gear portion 159b of second intermediate gear 158 is configured to be disposed in meshed engagement with output gear 160, e.g., linear gear rack 134 of drive bar 130, during a second portion "$S_2$" of the full output stroke length "$S_f$" of drive bar 130. That is, once drive bar 130 is moved distally beyond the first portion "$S_1$" to the second portion "$S_2$," linear gear rack 134 is moved into engagement with arcuate output gear portion 159b of second intermediate gear 158. During the first portion "$S_1$," linear gear rack 134 is disposed proximally of and out of engagement with arcuate output gear portion 159b of second intermediate gear 158.

In embodiments, the diameter of arcuate input gear portion 157a of first intermediate gear 156 is different than the diameter "$D_1$" of arcuate output gear portion 157b of first intermediate gear 158. Similarly, in embodiments, the diameter of arcuate input gear portion 159a of second intermediate gear 158 is different than the diameter "$D_2$" of arcuate output gear portion 159b of second intermediate gear 158. Further, the diameters of arcuate input gear portions 157a, 159a may be similar, in embodiments. The diameters "$D_1$" and "$D_2$" of arcuate output gear portions 157b, 159b, respectively, in embodiments, may be different, as detailed below.

With continued reference to FIGS. 1, 2, 5, and 6, and to FIGS. 5 and 6 in particular, as a result of the above-detailed configuration, pivoting of trigger 122 from the un-actuated position towards the actuated position rotates input gear 152 in a counter-clockwise direction (as viewed from the orientation shown in FIGS. 5 and 6). Counter-clockwise rotation of input gear 152, in turn, rotates transmission gear 154 in a clockwise direction (as viewed from the orientation shown in FIGS. 5 and 6), due to the meshed engagement between arcuate gear portion 128 of input gear 152 and arcuate input gear portion 155a of transmission gear 154. Clockwise rotation of transmission gear 154 rotates both first and second intermediate gears 156, 158 in a counter-clockwise direction (as viewed from the orientation shown in FIGS. 5 and 6), due to the meshed engagement between arcuate output gear portion 155b of transmission gear 154 and arcuate input gear portions 157a, 159a of first and second intermediate gears 156, 158, respectively.

During the first portion "$S_1$" of the full output stroke length "$S_f$" of drive bar 130, wherein arcuate output gear portion 157b of first intermediate gear 156 is disposed in meshed engagement with linear gear rack 134 of drive bar 130, the counter-clockwise rotation of first intermediate gear 156 translates drive bar 130 distally through body portion 111 of housing 110, while the counter-clockwise rotation of second intermediate gear 158 has no effect.

During the second portion "$S_2$" of the full output stroke length "$S_f$" of drive bar 130, wherein arcuate output gear portion 159b of second intermediate gear 158 is disposed in meshed engagement with linear gear rack 134 of drive bar 130, the counter-clockwise rotation of second intermediate gear 158 translates drive bar 130 distally through body portion 111 of housing 110, while the counter-clockwise rotation of first intermediate gear 156 has no effect.

The above-detailed distal advancement of drive bar 130, in response to actuation of trigger 122, occurs against the biasing of biasing member 140. As such, upon release of trigger 122, the bias of biasing member 140 pulls drive bar 130 proximally, thereby urging second intermediate gear 158 to rotate clockwise (as viewed from the orientation shown in FIGS. 5 and 6) during the second portion "$S_2$" of the full output stroke length "$S_f$" of drive bar 130 and urging first intermediate gear 156 to rotate clockwise (as viewed from the orientation shown in FIGS. 5 and 6) during the first portion "$S_1$" of the full output stroke length "$S_f$" of drive bar 130. The rotations of second and first intermediate gears 158, 156 each, in turn, rotates transmission gear 154 counter-clockwise (as viewed from the orientation shown in FIGS. 5 and 6) and, thus, first gear 152 clockwise (as viewed from the orientation shown in FIGS. 5 and 6), thereby returning trigger 122 towards the un-actuated position.

The above-detailed actuation mechanism 120 provides a compact configuration to enable use with reposable surgical clip applier 10 (FIGS. 1-2), wherein elongated assemblies, e.g., elongated assemblies 200, 300 (FIGS. 3 and 4), are releasably engagable with handle assembly 100 of reposable surgical clip applier 10 (FIGS. 1-2); however, actuation mechanism 120 is equally applicable for use with integrated surgical clip appliers and other configurations of surgical clip appliers.

The above-detailed actuation mechanism 120 is configured, as noted above, such that diameter "$D_1$" of arcuate output gear portion 157b of first intermediate gear 156 is different from diameter "$D_2$" of the arcuate output gear portion 159b of second intermediate gear 158. As such, a different mechanical advantage is provided during the first portion "$S_1$" of the full output stroke length "$S_f$" of drive bar 130 (and, thus, a corresponding first portion "$\alpha_1$" of an input rotation "$\alpha_f$" of trigger 122) as compared to the second portion "$S_2$" thereof (and, thus, a corresponding second portion "$\alpha_2$" of the input rotation "$\alpha_f$" of trigger 122). In embodiments, diameter "$D_1$" is greater than diameter "$D_2$" and the mechanical advantage during the first portion "$S_1$" is less than the mechanical advantage during the second portion "$S_2$." Such a configuration is advantageous at least because the greater mechanical advantage is provided during the second portion "$S_2$," where jaws of the end effector assembly of the elongated assembly are urged to a closed position relative to one another to fire the surgical clip, which requires greater force as compared to the first portion "$S_1$," where the surgical clip is loaded into the jaws. However, other configurations are also contemplated, depending upon the particular configuration of the elongated assembly utilized and the mechanical advantages sought.

In embodiments, the mechanical advantage provided during the first portion "$S_1$" of the full output stroke length "$S_f$" is 0.6 to 1.0, in embodiments, 0.7 to 0.9 and, in embodiments, about 0.8 (wherein the "about" takes into account manufacturing, material, environmental, and other tolerances). In embodiments, the mechanical advantage provided during the second portion "$S_2$" of the full output stroke length "$S_f$" is 3.5 to 4.0, in embodiments, 3.6 to 3.9 and, in embodiments, about 3.75 (wherein the "about" takes into account manufacturing, material, environmental, and other tolerances). In embodiments, the average mechanical advantage over the full output stroke length "$S_f$" is 1.65 to 1.8, in embodiments, 1.70 to 1.75, and, in embodiments, about 1.73 (wherein the "about" takes into account manufacturing, material, environmental, and other tolerances). In embodiments, the ratio of the mechanical advantage over second portion "$S_2$" of the full output stroke length "$S_f$" to the mechanical advantage over the first portion "$S_1$" of the full output stroke length "$S_f$" is 3 to 6, in embodiments, 4 to 5, and, in embodiments, 4.25 to 4.75.

The first and second portions "$S_1$" and "$S_2$" of the full output stroke length "$S_f$" may be equal, e.g., each corresponding to ½ of the full output stroke length "Se," or may be different. In embodiments, the first portion "$S_1$" defines ½ to ¾ of the full output stroke length "$S_f$," and, in embodiments, about ⅔ of the full output stroke length "$S_f$" (wherein the "about" takes into account manufacturing, material, environmental, and other tolerances). In embodiments, the second portion "$S_2$" defines ¼ to ½ of the full output stroke length "$S_f$," and, in embodiments, about ⅓ of the full output stroke length "$S_f$" (wherein the "about" takes into account manufacturing, material, environmental, and other tolerances).

In embodiments, the full output stroke length "$S_f$" is 1.0 inch to 1.4 inches, in embodiments, 1.1 inches to 1.3 inches, and, in embodiments, about 1.2 inches (wherein the "about" takes into account manufacturing, material, environmental, and other tolerances). In embodiments, the first portion "$S_1$" is 0.6 inches to 1.0 inch, in embodiments, 0.7 inches to 0.9 inches, and, in embodiments, about 0.8 inches (wherein the "about" takes into account manufacturing, material, environmental, and other tolerances). In embodiments, the second portion "$S_2$" is 0.2 inches to 0.6 inches, in embodiments, 0.3 inches to 0.5 inches, and, in embodiments, about 0.4 inches (wherein the "about" takes into account manufacturing, material, environmental, and other tolerances).

In embodiments, the full input rotation "$\alpha_f$" of trigger 122 is 35 to 45 degrees, in embodiments, 37.5 degrees to 42.5 degrees, and, in embodiments, about 40 degrees (wherein the "about" takes into account manufacturing, material, environmental, and other tolerances). The first and second portions "$\alpha_1$" and "$\alpha_2$" of the full input rotation "$\alpha_f$" of trigger 122 may be equal, e.g., each corresponding to ½ of the full input rotation "$\alpha_f$," or may be different. In embodiments, the first portion "$\alpha_1$" defines ¼ to ½ of the full input rotation "$\alpha_f$" and, in embodiments, about ⅓ of the full input rotation "$\alpha_f$" (wherein the "about" takes into account manufacturing, material, environmental, and other tolerances). In embodiments, the second portion "$\alpha_2$" defines ½ to ¾ of the full input rotation "$\alpha_f$"" and, in embodiments, about ⅔ of the full input rotation "$\alpha_f$" (wherein the "about" takes into account manufacturing, material, environmental, and other tolerances).

In embodiments, the first portion "$\alpha_1$" of the full input rotation "$\alpha_f$" is 7.5 degrees to 17.5 degrees, in embodiments, 10 degrees to 15 degrees, and, in embodiments, about 12.5 degrees (wherein the "about" takes into account manufacturing, material, environmental, and other tolerances). In embodiments, the second portion "$\alpha_2$" of the full input rotation "$\alpha_f$" is 22.5 degrees to 32.5 degrees, in embodiments, 25 degrees to 30 degrees, and, in embodiments, about 27.5 degrees (wherein the "about" takes into account manufacturing, material, environmental, and other tolerances).

The relative diameters of arcuate gear portion 128, arcuate input gear portion 155a, arcuate output gear portion 155b, arcuate input gear portion 157a, arcuate output gear portion 157b, arcuate input gear portion 159a, and arcuate output gear portion 159b are selected so as to achieve the desired first and second mechanical advantages, ratio therebetween, input rotations, and/or output stroke lengths, as detailed above.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. An actuation mechanism for a surgical clip applier, the actuation mechanism comprising:
    a drive bar movable through a stroke having a stroke length comprising a first portion and a second portion to fire at least one surgical clip, the drive bar including an output gear rack associated therewith;
    a trigger pivotable from an un-actuated position to an actuated position;
    a first intermediate gear including an input portion and an output portion, the input portion operably coupled to the trigger such that pivoting of the trigger from the un-actuated position to the actuated position rotates the first intermediate gear; and
    a second intermediate gear including an input portion and an output portion, the output portions of the first and second intermediate gears defining different diameters, the input portion of the second intermediate gear operably coupled to the trigger such that pivoting of the trigger from the un-actuated position to the actuated position rotates the second intermediate gear,
    wherein, in the first portion of the stroke length, the output portion of the first intermediate gear is disposed in direct meshed engagement with the gear rack and the output portion of the second intermediate gear is disengaged from the gear rack such that the first intermediate gear drives the drive bar along the first portion of the stroke length in response to pivoting of the trigger,
    wherein, in the second portion of the stroke length, the output portion of the second intermediate gear is disposed in direct meshed engagement with the gear rack and the output portion of the first intermediate gear is disengaged from the gear rack such that the second intermediate gear drives the drive bar along the second portion of the stroke length in response to pivoting of the trigger, and
    wherein a different mechanical advantage is provided in the first portion of the stroke length as compared to the second portion of the stroke length.

2. The actuation mechanism according to claim 1, wherein the mechanical advantage provided in the first portion of the stroke length is less than the mechanical advantage provided in the second portion of the stroke length.

3. The actuation mechanism according to claim 1, wherein the first portion of the stroke length is greater than the second portion of the stroke length.

4. The actuation mechanism according to claim 1, wherein the trigger is pivotable through an input rotation from the un-actuated position to the actuated position, the input rotation including a first portion corresponding to the first portion of the stroke length and a second portion corresponding to the second portion of the stroke length.

5. The actuation mechanism according to claim 4, wherein the first portion of the input rotation is less than the second portion of the input rotation.

6. The actuation mechanism according to claim 5, wherein the first portion of the stroke length is greater than the second portion of the stroke length.

7. The actuation mechanism according to claim 1, further comprising:
    an input gear associated with the trigger; and
    a transmission gear including an input portion and an output portion, the input portion of the transmission gear disposed in meshed engagement with the input gear and the output portion of the transmission gear disposed in meshed engagement with the input portions of the first and second intermediate gears.

8. A handle assembly of a surgical clip applier, comprising:
   a housing defining a body portion and a fixed handle portion extending from the body portion;
   a drive bar slidably supported within the body portion of the housing and movable relative thereto through a stroke having a stroke length comprising a first portion and a second portion to fire at least one surgical clip, the drive bar including an output gear rack associated therewith;
   a trigger pivotably connected to the housing and movable relative to the fixed handle portion thereof from an un-actuated position to an actuated position;
   a first intermediate gear including an input portion and an output portion, the input portion operably coupled to the trigger such that pivoting of the trigger from the un-actuated position to the actuated position rotates the first intermediate gear; and
   a second intermediate gear including an input portion and an output portion, the output portions of the first and second intermediate gears defining different diameters, the input portion of the second intermediate gear operably coupled to the trigger such that pivoting of the trigger from the un-actuated position to the actuated position rotates the second intermediate gear,
   wherein, in the first portion of the stroke length, the output portion of the first intermediate gear is disposed in direct meshed engagement with the gear rack and the output portion of the second intermediate gear is disengaged from the gear rack such that the first intermediate gear drives the drive bar along the first portion of the stroke length in response to pivoting of the trigger,
   wherein, in the second portion of the stroke length, the output portion of the second intermediate gear is disposed in direct meshed engagement with the gear rack and the output portion of the first intermediate gear is disengaged from the gear rack such that the second intermediate gear drives the drive bar along the second portion of the stroke length in response to pivoting of the trigger, and
   wherein a different mechanical advantage is provided in the first portion of the stroke length as compared to the second portion of the stroke length.

9. The handle assembly according to claim 8, wherein the mechanical advantage provided in the first portion of the stroke length is less than the mechanical advantage provided in the second portion of the stroke length.

10. The handle assembly according to claim 8, wherein the first portion of the stroke length is greater than the second portion of the stroke length.

11. The handle assembly according to claim 8, wherein the trigger is pivotable through an input rotation from the un-actuated position to the actuated position, the input rotation including a first portion corresponding to the first portion of the stroke length and a second portion corresponding to the second portion of the stroke length,
   wherein the first portion of the input rotation is less than the second portion of the input rotation, and the first portion of the stroke length is greater than the second portion of the stroke length.

12. The handle assembly according to claim 8, further comprising:
   an input gear associated with the trigger; and
   a transmission gear including an input portion and an output portion, the input portion of the transmission gear disposed in meshed engagement with the input gear and the output portion of the transmission gear disposed in meshed engagement with the input portions of the first and second intermediate gears.

13. The handle assembly according to claim 8, wherein the housing is configured to receive an elongated assembly supporting an end effector assembly at a distal end portion thereof, and wherein the drive bar is configured to operably interface with an actuation member of the elongated assembly.

14. A surgical clip applier, comprising:
   a handle assembly; and
   an elongated assembly extending distally from the handle assembly and supporting an end effector assembly at a distal end portion thereof, elongated assembly including an actuation member movable to fire at least one surgical clip from the end effector assembly,
   wherein the handle assembly includes:
      a housing defining a body portion and a fixed handle portion extending from the body portion;
      a drive bar slidably supported within the body portion of the housing and movable relative thereto through a stroke having a stroke length comprising a first portion and a second portion to fire at least one surgical clip, the drive bar including an output gear rack associated therewith;
      a trigger pivotably connected to the housing and movable relative to the fixed handle portion thereof from an un-actuated position to an actuated position;
      a first intermediate gear including an input portion and an output portion, the input portion operably coupled to the trigger such that pivoting of the trigger from the un-actuated position to the actuated position rotates the first intermediate gear; and
      a second intermediate gear including an input portion and an output portion, the output portions of the first and second intermediate gears defining different diameters, the input portion of the second intermediate gear operably coupled to the trigger such that pivoting of the trigger from the un-actuated position to the actuated position rotates the second intermediate gear,
   wherein, in the first portion of the stroke length, the output portion of the first intermediate gear is disposed in direct meshed engagement with the gear rack and the output portion of the second intermediate gear is disengaged from the gear rack such that the first intermediate gear drives the drive bar along the first portion of the stroke length in response to pivoting of the trigger,
   wherein, in the second portion of the stroke length, the output portion of the second intermediate gear is disposed in direct meshed engagement with the gear rack and the output portion of the first intermediate gear is disengaged from the gear rack such that the second intermediate gear drives the drive bar along the second portion of the stroke length in response to pivoting of the trigger, and
   wherein a different mechanical advantage is provided in the first portion of the stroke length as compared to the second portion of the stroke length.

15. The surgical clip applier according to claim 14, wherein the mechanical advantage provided in the first portion of the stroke length is less than the mechanical advantage provided in the second portion of the stroke length.

16. The surgical clip applier according to claim 14, wherein the first portion of the stroke length is greater than the second portion of the stroke length.

17. The surgical clip applier according to claim 14, wherein the trigger is pivotable through an input rotation from the un-actuated position to the actuated position, the input rotation including a first portion corresponding to the first portion of the stroke length and a second portion corresponding to the second portion of the stroke length.

18. The surgical clip applier according to claim 17, wherein the first portion of the input rotation is less than the second portion of the input rotation, and the first portion of the stroke length is greater than the second portion of the stroke length.

19. The surgical clip applier according to claim 14, further comprising:
   an input gear associated with the trigger; and
   a transmission gear including an input portion and an output portion, the input portion of the transmission gear disposed in meshed engagement with the input gear and the output portion of the transmission gear disposed in meshed engagement with the input portions of the first and second intermediate gears.

20. The surgical clip applier according to claim 14, wherein the elongated assembly is releasably engagable with the handle assembly.

\* \* \* \* \*